(12) United States Patent
Mandala et al.

(10) Patent No.: US 6,437,165 B1
(45) Date of Patent: Aug. 20, 2002

(54) PHOSPHATE DERIVATIVES AS IMMUNOREGULATORY AGENTS

(75) Inventors: Suzanne Mandala, Scotch Plains; James Bergstrom, Neshanic Station; Richard Hajdu, Old Bridge; Hugh Rosen, Springfield; William Parsons, Belle Mead; Deborah J. Card, Somerset; Malcolm Maccoss, Freehold; Rupprecht Kathleen, Cranford, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/942,411

(22) Filed: Aug. 30, 2001

Related U.S. Application Data
(60) Provisional application No. 60/229,438, filed on Aug. 31, 2000.

(51) Int. Cl.[7] .............................................. A61K 31/662
(52) U.S. Cl. ........................ 558/169; 558/70; 558/166; 514/114
(58) Field of Search ......................... 558/70, 166, 169; 514/114

(56) References Cited

U.S. PATENT DOCUMENTS

| | | |
|---|---|---|
| 3,726,948 A | 4/1973 | Botts |
| 5,604,229 A | 2/1997 | Fujita et al. |
| 5,719,176 A | 2/1998 | Jujita et al. |
| 5,948,820 A | 9/1999 | Jujita et al. |
| 5,952,316 A | 9/1999 | Fujita et al. |
| 6,004,565 A | 12/1999 | Chiba et al. |
| 6,121,329 A | 9/2000 | Jujii et al. |
| 6,197,829 B1 | 3/2001 | Fujii et al. |
| 6,274,629 B1 | 8/2001 | Cottens et al. |
| 6,277,888 B1 | 8/2001 | Sakai et al. |
| 6,284,915 B2 | 9/2001 | Hirase et al. |
| 2001/0008945 A1 | 7/2001 | Hirase et al. |

FOREIGN PATENT DOCUMENTS

| | | |
|---|---|---|
| EP | 0 812 588 A1 | 12/1997 |
| EP | 0 989 113 A1 | 3/2000 |
| EP | 1 050 301 A1 | 11/2000 |
| JP | 10-147587 | 6/1998 |
| JP | 11-034300 | 2/1999 |
| JP | 11-310556 | 11/1999 |
| WO | WO98/03162 | 1/1998 |
| WO | WO98/22100 | 5/1998 |
| WO | WO00/27798 | 5/2000 |

OTHER PUBLICATIONS

V. Brinkmann, et al.; Tranplantation 72, 764–9 (2001).
H. H. Neumayer, et al., Transplantation 67, S204 (1999).
L. Maier, Phosphorus, Sulfur Silicon Retal. Elem., vol. 56 (1–4), pp. 5–15, 1991.
Fukuoka, Pharm. Res Yoshitomi Pharm. Ind., Ltd.; 871–8550, 26(3), 287–303 (1998).
Kiuchi, et al.; J. Med. Chem., 43, 2946–2961 (2000).
F. J. Dumont, Curr. Opin. Anti–Inflammatory Immunomodulatory Invest. Drugs (2000), 2(4), 314–331.

*Primary Examiner*—Floyd D. Higel
*Assistant Examiner*—Kamal Saeed
(74) *Attorney, Agent, or Firm*—Raynard Yuro; David L. Rose

(57) ABSTRACT

Immunoregulatory compounds are disclosed of the formula:

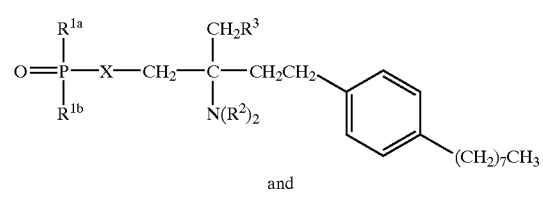

and

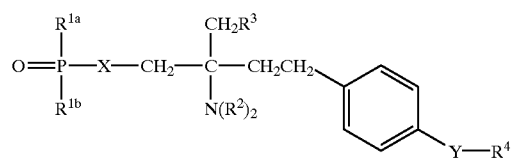

as well as the pharmaceutically acceptable salts and hydrates thereof, are disclosed. The compounds are useful for treating immune mediated diseases and conditions, such as bone marrow, organ and tissue transplant rejection.

Pharmaceutical compositions and methods of use are included.

38 Claims, No Drawings

PHOSPHATE DERIVATIVES AS IMMUNOREGULATORY AGENTS

CROSS-REFERENCE TO RELATED APPLICATIONS

This application claims the benefit of U.S. Provisional Application No. 60/229,438 filed on Aug. 31, 2000.

BACKGROUND OF THE INVENTION

The present invention is related to chemical compounds that have immunoregulatory activity, pharmaceutical compositions containing such compounds and methods of treatment or prevention.

Immunoregulatory abnormalities have been shown to exist in a wide variety of autoimmune and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, autoimmune myositis, Wegener's granulomatosis, ichthyosis, Graves ophthalmopathy and asthma.

Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates. Similarly, following a bone-marrow or an organ transplantation, the host lymphocytes recognize the foreign tissue antigens and begin to produce both cellular and humoral responses including antibodies, cytokines and cytotoxic lymphocytes which lead to graft rejection.

One end result of an autoimmune or a rejection process is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb to infection as they are to their autoimmune disease.

Cyclosporin A is a drug used to prevent rejection of transplanted organs. FK-506 is another drug approved for the prevention of transplant organ rejection, and in particular, liver transplantation. Cyclosporin A and FK-506 act by inhibiting the body's immune system from mobilizing its vast arsenal of natural protecting agents to reject the transplant's foreign protein. Cyclosporin A was approved for the treatment of severe psoriasis and has been approved by European regulatory agencies for the treatment of atopic dermatitis.

Though they are effective in delaying or suppressing transplant rejection, Cyclosporin A and FK-506 are known to cause several undesirable side effects including nephrotoxicity, neurotoxicity, and gastrointestinal discomfort. Therefore, an immunosuppressant without these side effects still remains to be developed and would be highly desirable.

While the main use for immunosuppressants is in treating bone marrow, organ and transplant rejection, other uses for such compounds include the treatment of arthritis, in particular, rheumatoid arthritis, insulin and non-insulin dependent diabetes, multiple sclerosis, psoriasis, inflammatory bowel disease, Crohn's disease, lupus erythematosis and the like.

Thus, the present invention is focused on providing immunosuppressant compounds that are safer and more effective than prior compounds, having a better safety profile. These and other objects will be apparent to those of ordinary skill in the art from the description contained herein.

SUMMARY OF THE INVENTION

The present invention relates to a compound represented by formula 1:

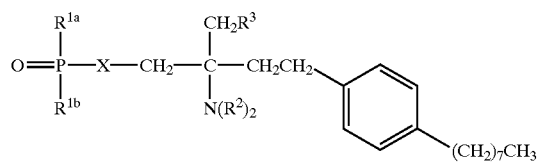

as well as the pharmaceutically acceptable salts and hydrates thereof, wherein:

X is O, S, $NR^1$ or $(CH_2)_{1-2}$, optionally substituted with 1–4 halo groups;

$R^1$ is H, $C_{1-4}$ alkyl or $haloC_{1-4}$ alkyl;

$R^{1a}$ is H, OH, $C_{1-4}$ alkyl, or $OC_{1-4}$ alkyl, the alkyl and alkyl portions being optionally substituted with 1–3 halo groups;

$R^{1b}$ represents H, OH, $C_{1-4}$ alkyl or $haloC_{1-4}$ alkyl;

each $R^2$ is H, $C_{1-4}$ alkyl or $haloC_{1-4}$ alkyl; and $R^3$ is H, OH, halo, $OC_{1-4}$ alkyl or $O-haloC_{1-4}$ alkyl.

The invention also relates to compounds represented by formula A:

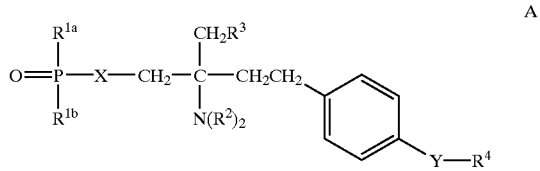

or a pharmaceutically acceptable salt or hydrate thereof, wherein:

X is O, S, $NR^1$ or $(CH_2)_{1-2}$, optionally substituted with 1–4 halo groups;

$R^1$ is H, $C_{1-4}$ alkyl or $haloC_{1-4}$ alkyl;

$R^{1a}$ is H, OH, $C_{1-4}$ alkyl, or $OC_{1-4}$ alkyl, the alkyl and alkyl portions being optionally substituted with 1–3 halo groups;

$R^{1b}$ represents H, OH, $C_{1-4}$ alkyl or $haloC_{1-4}$ alkyl;

$R^2$ is H, $C_{1-4}$ alkyl or $haloC_{1-4}$ alkyl, $R^3$ is H, OH, halo, $C_{1-4}$alkyl, $OC_{1-4}$alkyl, $O-haloC_{1-4}$alkyl or $hydroxyC_{1-4}$alkyl, Y is selected from the group consisting of: $—CH_2—$, $—C(O)—$, $—CH(OH)—$, $—C(=NOH)—$, O and S, and $R^4$ is selected from the group consisting of: $C_{4-14}$alkyl and $C_{4-14}$alkenyl.

Pharmaceutical compositions and methods of treatment are also included.

DETAILED DESCRIPTION OF THE INVENTION

As used herein the following terms are defined as set forth below unless otherwise indicated.

Alkyl includes straight as well as branched alkyl groups containing the indicated number of carbon atoms.

Halo includes F, Cl, I and Br.

Haloalkyl represents a straight or branched alkyl group substituted with at least one halo group, and being optionally substituted with up to the maximum number of halo groups.

The present invention relates to a compound represented by formula 1:

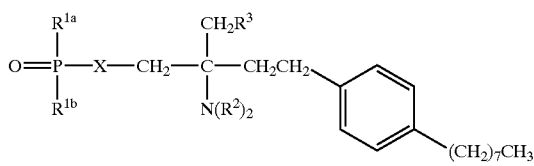

as well as the pharmaceutically acceptable salts and hydrates thereof, wherein:

X is O, S, $NR^1$ or $(CH_2)_{1-2}$, optionally substituted with 1–4 halo groups;

$R^1$ is H, $C_{1-4}$ alkyl or halo$C_{1-4}$ alkyl;

$R^{1a}$ is H, OH, $C_{1-4}$ alkyl, or $OC_{1-4}$ alkyl, the alkyl and alkyl portions being optionally substituted with 1–3 halo groups;

$R^{1b}$ represents H, OH, $C_{1-4}$ alkyl or halo$C_{1-4}$ alkyl;

each $R^2$ is H, $C_{1-4}$ alkyl or halo$C_{1-4}$ alkyl; and $R^3$ is H, OH, halo, $OC_{1-4}$ alkyl or O-halo$C_{1-4}$ alkyl.

In one aspect of the invention that is of particular interest, a compound of formula 1 is provided wherein X is O or $(CH_2)_{1-2}$, optionally substituted with 1–4 halo groups. Within this subset, all other variables are as originally defined.

More particularly, an aspect of the invention that is of particular interest relates to compounds of formula 1 wherein X is O or $CH_2$. Within this subset, all other variables are as originally defined.

Even more particularly, an aspect of the invention that is interest relates to compounds of formula 1 wherein X is O. Within this subset, all other variables are as originally defined.

In another aspect of the invention that is of particular interest, a compound of formula 1 is provided wherein $R^{1a}$ is H or OH. Within this subset, all other variables are as originally defined.

In another aspect of the invention that is of particular interest, a compound of formula 1 is provided wherein $R^{1b}$ represents H or OH. Within this subset, all other variables are as originally defined.

In another aspect of the invention that is of particular interest, a compound of formula 1 is provided wherein $R^3$ is H, OH, halo, $OC_{1-4}$ alkyl or O-halo$C_{1-4}$ alkyl. Within this subset, all other variables are as originally defined.

In another aspect of the invention that is of particular interest, a compound of formula 1 is provided wherein $R^2$ is H or $C_{1-4}$ alkyl. Within this subset, all other variables are as originally defined.

A group of compounds that is of particular interest is described in connection with formula 1 wherein:

X is O or $(CH_2)_{1-2}$, optionally substituted with 1–4 halo groups;

$R^{1a}$ is H or OH;

$R^{1b}$ represents H or OH;

$R^2$ is H, $C_{1-4}$ alkyl or halo$C_{1-4}$ alkyl, and $R^3$ is H, OH, halo, $OC_{1-4}$ alkyl or O-halo$C_{1-4}$ alkyl.

Preferred compounds of the present invention include the following:

TABLE 1

1a $$O=\underset{OH}{\overset{OH}{P}}-X-CH_2-\underset{N(R^2)_2}{\overset{CH_2R^3}{C}}-CH_2CH_2-\text{—Ar}(CH_2)_7CH_3$$

| Cpd | X | $R^2/R^2$ | $R^3$ |
|-----|---|-----------|-------|
| 1 | O | H/H | OH |
| 2 | $CH_2$ | H/H | OH |
| 3 | $CH_2CH_2$ | H/H | OH |
| 4 | O | H/$CH_3$ | OH |
| 5 | $CH_2$ | H/$CH_3$ | OH |
| 6 | $CH_2CH_2$ | H/$CH_3$ | OH |
| 7 | O | $CH_3/CH_3$ | OH |
| 8 | $CH_2$ | $CH_3/CH_3$ | OH |
| 9 | $CH_2CH_2$ | $CH_3/CH_3$ | OH |
| 10 | O | H/H | H |
| 11 | $CH_2$ | H/H | H |
| 12 | $CH_2CH_2$ | H/H | H |
| 13 | O | H/$CH_3$ | H |
| 14 | $CH_2$ | H/$CH_3$ | H |
| 15 | $CH_2CH_2$ | H/$CH_3$ | H |
| 16 | O | $CH_3/CH_3$ | H |
| 17 | $CH_2$ | $CH_3/CH_3$ | H |
| 18 | $CH_2CH_2$ | $CH_3/CH_3$ | H |

The invention described herein includes pharmaceutically acceptable salts and hydrates. Pharmaceutically acceptable salts include both the metallic (inorganic) salts and organic salts; a list of which is given in *Remington's Pharmaceutical Sciences,* 17th Edition, pg. 1418 (1985). It is well known to one skilled in the art that an appropriate salt form is chosen based on physical and chemical stability, flowability, hydroscopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or pamoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I.

The invention also includes the compounds falling within formula 1 in the form of one or more stereoisomers, in substantially pure form or in the form of a mixture of stereoisomers. All such isomers are encompassed within the present invention.

Immunoregulatory agents as used herein include compounds that act to suppress the immune system in instances where immunosuppression is in order, such as in bone marrow, organ or transplant rejection, autoimmune and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma.

More particularly, the compounds of the present invention are useful to treat or prevent a disease or disorder selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatoses, seborrheic dermatitis, Lichen planus, Pemphigus, bullous pemphigoid, Epidermolysis bullosa, urticaria, angioedemas, vasculitis, erythema, cutaneous eosinophilia, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal bums, Coeliac diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy; Pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis, pigentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

Also embodied within the present invention is a method of preventing or treating resistance to transplantation or transplantation rejection of organs or tissues in a mammalian patient in need thereof, which comprises administering a therapeutically effective amount of the compound of Formula 1.

A method of suppressing the immune system in a mammalian patient in need thereof, which comprises administering to the patient an immune system suppressing amount of the compound of Formula 1 is yet another embodiment.

Most particularly, the method described herein encompasses a method of treating or preventing bone marrow or organ transplant rejection which is comprised of admininstering to a mammalian patient in need of such treatment or prevention a compound of formula 1, or a pharmaceutically acceptable salt or hydrate thereof, in an amount that is effective for treating or preventing bone marrow or organ transplant rejection.

The present invention also includes a pharmaceutical formulation comprising a pharmaceutically acceptable carrier and the compound of Formula 1 or a pharmaceutically acceptable salt or hydrate thereof. A preferred embodiment of the formulation is one where a second immunosuppressive agent is also included. Examples of such second immunosuppressive agents are, but are not limited to azathioprine, brequinar sodium, deoxyspergualin, mizaribine, mycophenolic acid morpholino ester, cyclosporin, FK-506 and rapamycin.

Methods for preparing the compounds of this invention are illustrated in the following schemes and examples. Alternative routes will be easily discernible to practitioners in the field.

Reaction Scheme 1

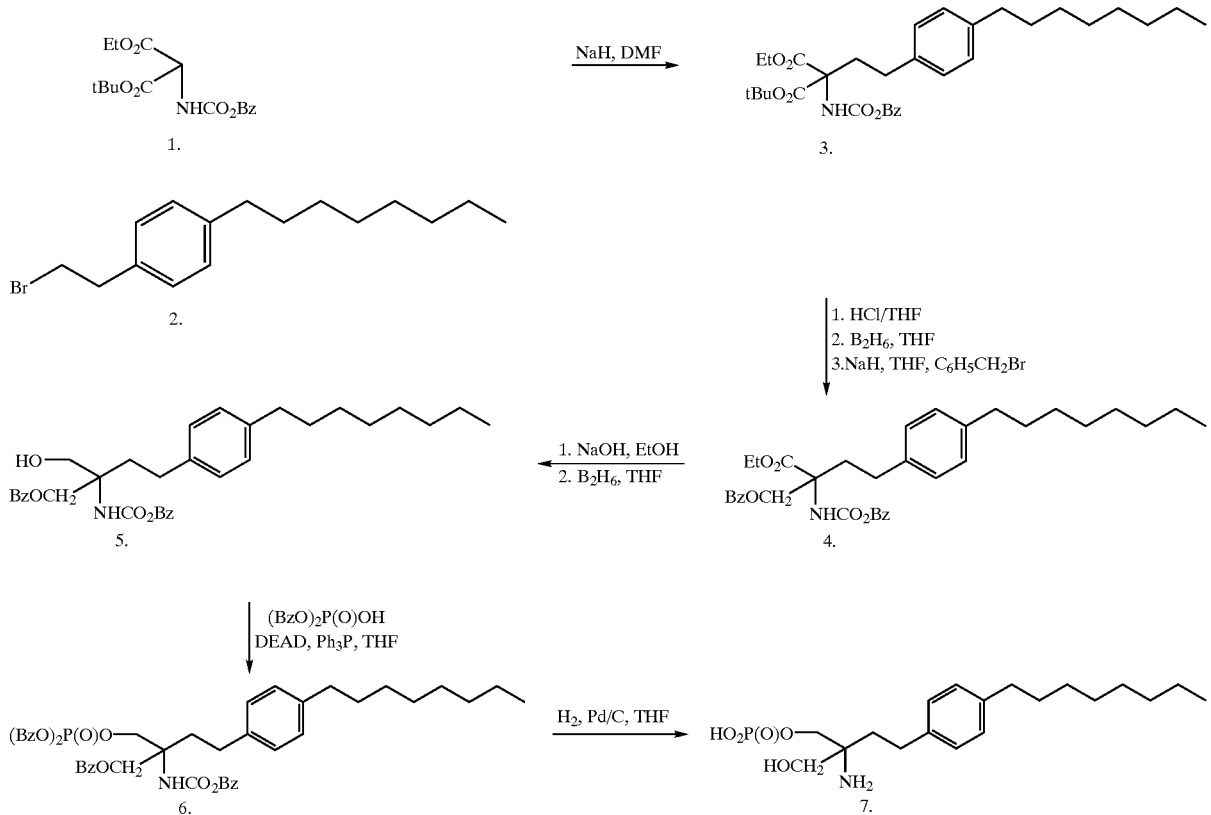

In Reaction Scheme 1, the differentially protected amino malonate 1 is reacted with bromide 2 and sodium hydride in DMF as described by Kiuche et. al. [J. Medicinal Chemistry 43, 2946–2961 (2000) and references cited therein] to provide compound 3. The t-butyl ester of compound 3 can be removed with HCl in a solvent such as THF to give the corresponding carboxylic acid. The 15 acid is then reduced to the alcohol with diborane in THF (see March, J. "Advanced Organic Chemistry", 4$^{th}$ ed., John Wiley & Sons, New York pp. 1208, 1214–1215). The alcohol can be converted to its benzyl ether 4 by several commonly used methods. One method is to react the alcohol with benzyl bromide and sodium hydride in a solvent such as THF. The ethyl ester of compound 4 is hydrolyzed to acid 5 by reaction with sodium hydroxide in a solvent mixture of ethanol and water. Compound 5 is converted to dibenzyl phosphonate 6 by a Mitsunobu reaction. A mixture of compound 5, dibenzylphosphate, triphenylphosphine and diethylazodicarboxylate (DEAD) in THF leads to compound 6. (see March, J. "Advanced Organic Chemistry", 4$^{th}$ ed., John Wiley & Sons, New York pp. 395–396). Removal of the benzyl protecting groups by hydrogenolysis gives the phosphate ester 7.

Reaction Scheme 2

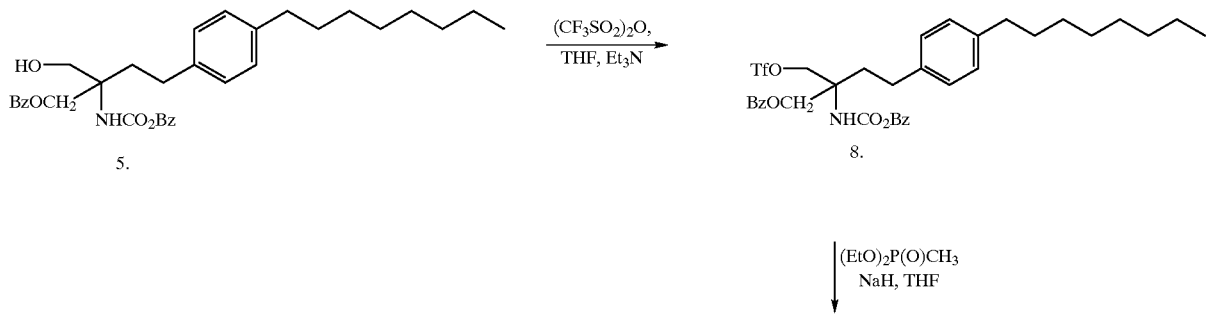

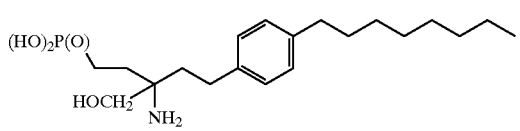 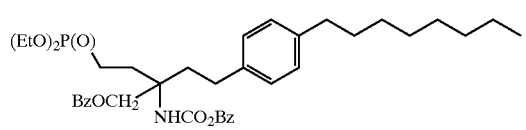

In Reaction Scheme 2, a method is provided for the synthesis of phosphonate analogs. The hydroxy group of compound 5 (Reaction Scheme 1) is converted to a leaving group. In his scheme, compound 5 is reacted with triflic anhydride and triethylamine in a solvent such as THF to give the triflate ester 8. Other leaving groups such as a methanesulfonate, or p-toluene sulfonate esters or a halide can also be prepared by commonly known methods. Triflate 8 is then reacted with diethylmethylphosphonate anion in THF to give the protected phosphonate derivative 9. In this reaction, diethylmethylphosphonate in THF at reduced temperature is deprotonated with a base such as sodium hydride or lithium diisopropylamine in a solvent such as THF and this mixture is then reacted with compound 8 to give compound 9. Deprotection of compound 9 to give phosphonate derivative 10 is completed in two steps. One first hydrolyzes the diethyl ester under acidic or basic conditions. In this scheme, compound 9 is stirred with HCl in a mixture of ethanol and water, heating if necessary. Alternatively, one can stir compound 9 with sodium hydroxide in the same solvent mixture. Finally, the benzyl groups are removed by hydrogenation as described in Reaction Scheme 1.

The present compounds, including salts and hydrates thereof, are useful in the treatment of autoimmune diseases, including the prevention of rejection of bone marrow transplant, foreign organ transplants and/or related afflictions, diseases and illnesses.

The compounds of this invention can be administered by any means that effects contact of the active ingredient compound with the site of action in the body of a warm-blooded animal. For example, administration, can be oral, topical, including transdernmal, ocular, buccal, intranasal, inhalation, intravaginal, rectal, intracistemal and parenteral. The term "parenteral" as used herein refers to modes of administration which include subcutaneous, intravenous, intramuscular, intraarticular injection or infusion, intrasternal and intraperitoneal.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.1–500 milligrams per day. Ordinarily, from 10 to 100 milligrams per day in one or more applications is effective to obtain desired results. These dosages are the effective amounts for the treatment of autoimmune diseases, the prevention of rejection of foreign organ transplants and/or related afflictions, diseases and illnesses.

The active ingredient can be administered orally in solid dosage forms, such as capsules, tablets, troches, dragees, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences,* A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

EXAMPLE ONE

The compound 2-amino-2-[-(4-octylphenyl)ethyl]propane-1,3-diol hydrochloride is combined with whole blood from laboratory mice. Compound 1 of Table 1 is produced. This compound has immunosuppressant activity as measured using the procedures set forth in J. Immunology 2000, 164: 5761–5770, incorporated herein by reference.

The present invention also relates to compounds represented by Formula A:

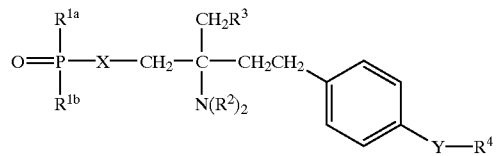

or a pharmaceutically acceptable salt or hydrate thereof, wherein:

X is O, S, $NR^1$ or $(CH_2)_{1-2}$, optionally substituted with 1–4 halo groups;

$R^1$ is H, $C_{1-4}$ alkyl or halo$C_{1-4}$ alkyl;

$R^{1a}$ is H, OH, $C_{1-4}$ alkyl, or $OC_{1-4}$ alkyl, the alkyl and alkyl portions being optionally substituted with 1–3 halo groups;

$R^{1b}$ represents H, OH, $C_{1-4}$ alkyl or halo$C_{1-4}$ alkyl;

each $R^2$ is independently selected from the group consisting of: H, $C_{1-4}$ alkyl and halo$C_{1-4}$ alkyl, $R^3$ is H, OH, halo, $C_{1-4}$alkyl, $OC_{1-4}$alkyl, O-halo$C_{1-4}$alkyl or hydroxy$C_{1-4}$alkyl, Y is selected from the group consisting of: —$CH_2$—, —C(O)—, —CH(OH)—, —C(=NOH)—, O and S, and $R^4$ is selected from the group consisting of: $C_{4-14}$alkyl and $C_{4-14}$alkenyl.

In one aspect of the invention that is of particular interest, a compound of formula A is provided wherein X is O or $(CH_2)_{1-2}$, optionally substituted with 1–4 halo groups. Within this subset, all other variables are as originally defined.

More particularly, an aspect of the invention that is of particular interest relates to compounds of formula A wherein X is O or $CH_2$. Within this subset, all other variables are as originally defined.

Even more particularly, an aspect of the invention that is interest relates to compounds of formula A wherein X is O. Within this subset, all other variables are as originally defined.

In another aspect of the invention that is of particular interest, a compound of formula A is provided wherein $R^{1a}$ is H or OH. Within this subset, all other variables are as originally defined.

In another aspect of the invention that is of particular interest, a compound of formula A is provided wherein $R^{1b}$ represents H or OH. Within this subset, all other variables are as originally defined.

In another aspect of the invention that is of particular interest, a compound of formula A is provided wherein $R^3$ is H, OH, halo, $OC_{1-4}$ alkyl or O-halo$C_{1-4}$ alkyl. Within this subset, all other variables are as originally defined.

In another aspect of the invention that is of particular interest, a compound of formula A is provided wherein $R^2$ is H or $C_{1-4}$ alkyl. Within this subset, all other variables are as originally defined.

Another embodiment of the invention encompasses compounds of Formula A wherein:

X is O or $(CH_2)_{1-2}$, optionally substituted with 1–4 halo groups;

$R^{1a}$ is H or OH;

$R^{1b}$ represents H or OH;

each $R^2$ is independently selected from the group consisting of: H, $C_{1-4}$ alkyl and halo$C_{1-4}$ alkyl, and $R^3$ is H, OH, halo, $C_{1-4}$alkyl, $OC_{1-4}$alkyl, O-halo$C_{1-4}$alkyl or hydroxy$C_{1-4}$alkyl.

Another embodiment of the invention encompasses compounds of Formula A wherein Y is —CH$_2$— and R$^4$ is heptyl. Within this embodiment is encompassed a compound of Formula A wherein:

X is O or CH$_2$, optionally substituted with 1–2 halo groups;

R$^{1a}$ is OH;

R$^{1b}$ is OH;

each R$^2$ is H, and

R$^3$ is H or OH.

The invention also encompasses a compound selected from the group consisting of:

(a) 3-Amino-3-hydroxymethyl-5-(4-octylphenyl) pentylphosphonic acid;

(b) 3-Amino-3-methyl-5-(4-(octyl)phenyl) pentylphosphonic acid; and (c) 1,1-Difluoro-3-amino-3-hydroxymethyl-5-(4-octylphenyl) pentylphosphonic acid.

In another embodiment, the invention encompasses a compound which is 2-Amino-2-phosphoryloxymethyl-4-(4-(octyl)phenyl)butanol.

In another embodiment, the invention encompasses a compound which is (R)-2-Amino-2-phosphoryloxymethyl-4-(4-(octyl)phenyl)butanol.

In another embodiment, the invention encompasses a compound which is (S)-2-Amino-2-phosphoryloxymethyl-4-(4-(octyl)phenyl)butanol.

Preferred salts of this invention for the reasons cited above include potassium, sodium, calcium and ammonium salts. Also included within the scope of this invention are crystal forms, hydrates and solvates of the compounds of Formula A.

The invention also includes the compounds falling within formula A in the form of one or more stereoisomers, in substantially pure form or in the form of a mixture of stereoisomers. All such isomers are encompassed within the present invention.

The invention also includes a method of treating or preventing an immunoregulatory abnormality in a mammalian patient in need of such treatment or prevention, comprising administering to said patient a compound of formula A in an amount that is effective for treating or preventing said immunoregulatory abnormality.

More particularly, the invention encompasses the above method wherein the immunoregulatory abnormality is an autoimmune or chronic inflammatory disease selected from the group consisting of: systemic lupus erythematosis, chronic rheumatoid arthritis, type I and II diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma.

Another embodiment encompasses the above method wherein the immunoregulatory abnormality is bone marrow or organ transplant rejection.

Another embodiment encompasses the above method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, Lichen planus, Pemphigus, bullous pemphigoid, Epidermolysis bullosa, urticaria, angioedemas, vasculitis, erythema, cutaneous eosinophilia, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischernic diseases and thrombosis, ischemic bowel diseases, inflammatory bowel diseases, necrotizing enterocolitis, intestinal lesions associated with thermal burns, Coeliac diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy; Pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis, pigentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C$_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

The invention also encompasses a method of suppressing the immune system in a mammalian patient in need of immunosuppression comprising administering to said patient an immunosuppressing effective amount of a compound of formula A.

The present invention also includes a pharmaceutical formulation comprising a pharmaceutically acceptable carrier and the compound of Formula A or a pharmaceutically acceptable salt or hydrate thereof. A preferred embodiment of the formulation is one where a second immunosuppressive agent is also included. Examples of such second immunosuppressive agents are, but are not limited to azathioprine, brequinar sodium, deoxyspergualin, mizaribine, mycophenolic acid morpholino ester, cyclosporin, FK-506 and rapamycin.

Additional methods for preparing the compounds of this invention are illustrated in the following schemes and examples. Alternative routes will be easily discernible to practitioners in the field.

Compounds in the present invention in which $R_{1a}=R_{1b}=$ OH, $R_2=H$, $R_3=H$ and $X=$—$CH_2$— can be prepared as shown in Scheme 3. Triethyl 4-phosphonobutyrate can be treated with a strong, hindered base (e.g., lithium diisopropylamide (LDA), sodium bis(trimethylsilyl)amide (NaHMDS), potassium bis(trimethylsilyl)amide (KHMDS) in an ethereal solvent (e.g., diethyl ether, dimethoxyethane (DME), tetrahydrofuran (THF) under anhydrous conditions at or below 0° C. followed by treatment with an arylethyl bromide, iodide or trifluoromethanesulfonate ester. After a second alkylation carried out similarly, but employing iodomethane as the alkylating agent, compound A is obtained. Saponification of the ethyl ester of A can afford carboxylic acid B. Hydrolysis of A under acidic conditions can also afford B. The carboxy group of B can be converted to an isocyanate (Curtius rearrangement) by first treating B with an alkyl chloroformate and tertiary amine base in THF to afford a mixed anhydride followed by treatment with sodium azide in aqueous acetone or aqueous THF followed by heating at or above 60° C. in an inert solvent (e.g. benzene or toluene) to give the isocyanate. Alternatively, B could first be activated as an acid chloride (e.g., by treating it with oxalyl chloride and catalytic N,N-dimethylformamide (DMF) in methylene chloride ($CH_2Cl_2$) or by treating it with thionyl chloride in $CH_2Cl_2$). The isocyanate is reacted with an alcohol ($R_aOH$) to afford carbamate C. After treating C with trimethylsilyl bromide (TMS-Br) or trimethylsilyl iodide (TMS-I) in a suitable solvent ($CH_2Cl_2$, chloroform ($CHCl_3$), acetonitrile ($CH_3CN$), D is obtained.

Scheme 3

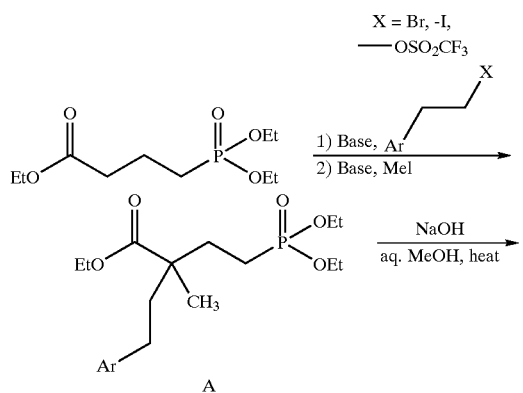

Compounds in the present invention in which $R_{1a}=R_{1a}=$ OH, $R_2=H$, $R_3=$—OH and $X=O$ can be prepared as shown in Scheme 4. The amino group of E (which can be prepared using the methods analogous to those described in Kiuchi, et.al. *Journal of Medicinal Chemistry*, 2000, 43, 2946–2961) can be protected by treating it with an alkyl chloroformate or a dialkyl dicarbonate in an appropriate solvent to afford carbamate F. Benzylidene acetal G is obtained by warming F and benzaldehyde in the presence of an acid catalyst (e.g., p-toluenesulfonic acid, methanesulfonic acid) in a solvent that would allow for the azeotropic removal of water (e.g., benzene, toluene). Treating G with a reducing agent such as borane, dimethylamine complex/boron trifluoride etherate or diisobutylaluminum hydride in an appropriate solvent ($CH_2Cl_2$, toluene) can afford benzyl ether H. Phosphorylation can be carried out by treating H with a N,N-dialkylamino dialkylphosphite (e.g., diethylamino dibenzylphosphite, diisopropylamino dibenzylphosphite) and catalytic 1H-tetrazole in an appropriate solvent (e.g., $CH_2Cl_2$, acetonitrile) followed by an oxidizing agent (e.g., 3-chloro peroxybenzoic acid, peracetic acid, 4-methylmorpholine N-oxide) to give phosphate ester I. Removal of the protecting groups of I can afford phosphate J. In cases where $R_a=R_b=$—$CH_2Ph$, this can be done by treating I with sodium in liquid ammonia. Alternatively, this can be done by stirring I in a solution of water and alcohol (e.g., methanol, ethanol) in the presence of palladium or platinum catalyst under an atmosphere of hydrogen gas.

Scheme 4

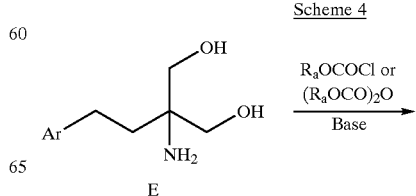

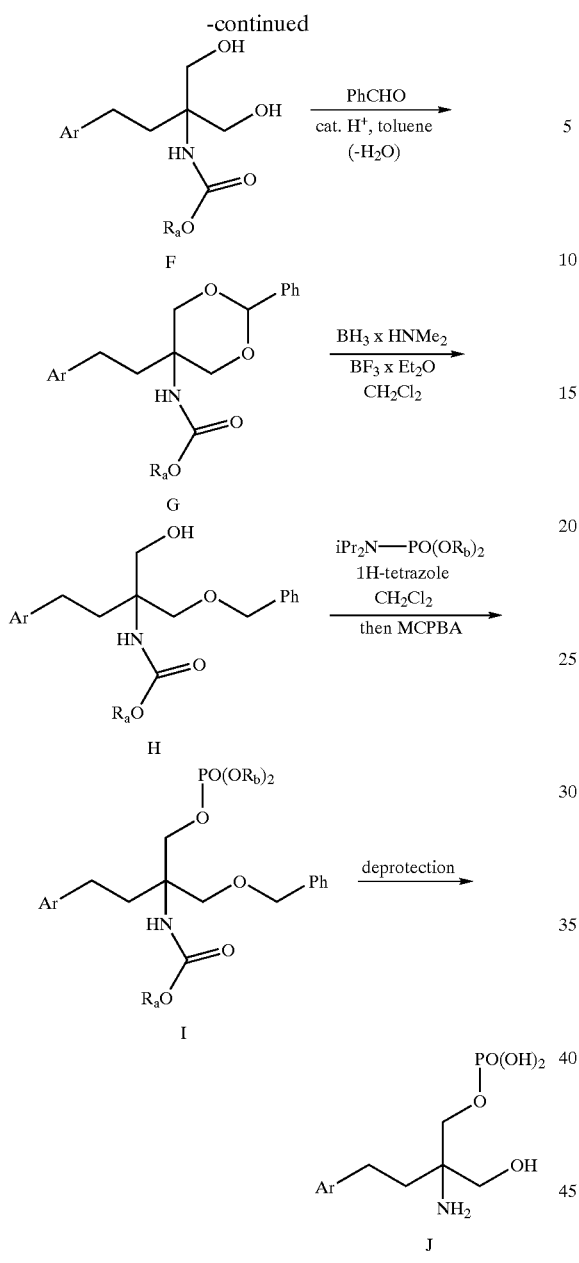

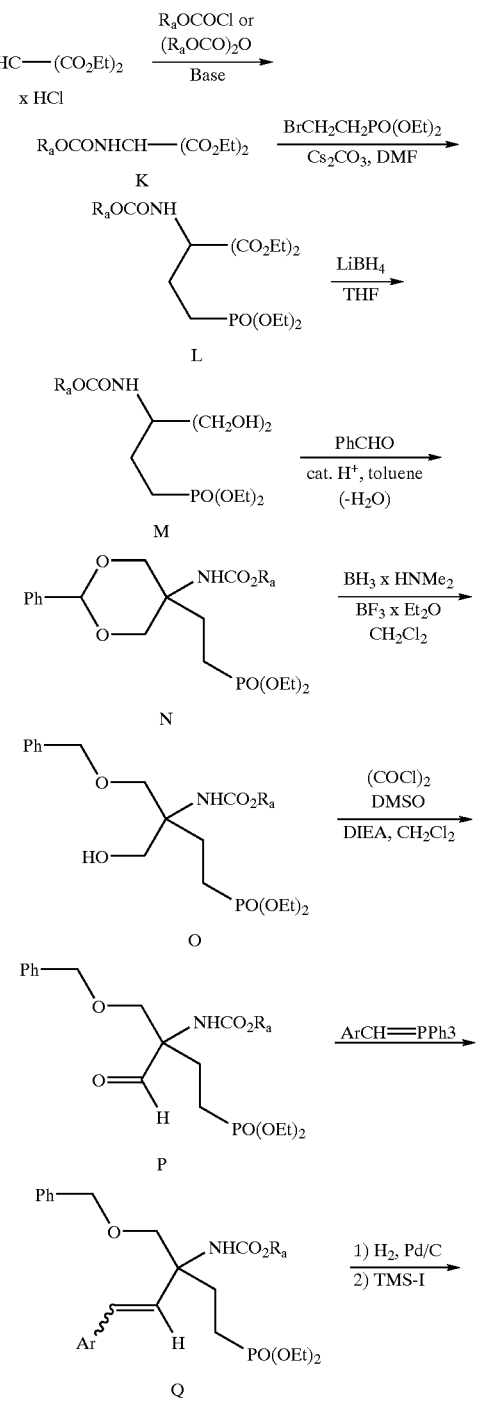

Compounds in the present invention in which $R_{1a}=R_{1b}=$ OH, $R_2=H$, $R_3=OH$ and $X=-CH_2-$ can be prepared as shown in Scheme 5. The amino group of amino diethylmalonate can be protected by treating it with an alkyl chloroformate or a dialkyl dicarbonate in an appropriate solvent to afford carbamate K. Alkylation of K with diethyl 2-bromoethylphosphonate in DMF in the presence of base (e.g., cesium carbonate, potassium carbonate, sodium hydride) can afford L. Treatment of L with a reducing agent in an appropriate solvent (lithium borohydride in THF or DME; diisobutyl aluminum hydride in $CH_2Cl_2$ or toluene) can afford diol M. Benzylidene acetal N is obtained by warming M and benzaldehyde in the presence of an acid catalyst (e.g., p-toluenesulfonic acid, methanesulfonic acid) in a solvent that would allow for the azeotropic removal of water (e.g., benzene, toluene). Treating N with a reducing agent such as borane, dimethylamine complex/boron trifluoride etherate or diisobutylaluminum hydride in an appropriate solvent ($CH_2Cl_2$, toluene) can afford benzyl ether O.

Oxidation under Swern conditions (oxalyl chloride/DMSO in $CH_2Cl_2$ at low temperature (<-40° C.) followed by a trialkylamine base and warming to ambient temperature) affords aldehyde P. Reacting aldeyde P with a Wittig reagent affords alkene Q. Reduction of the double bond of Q can be carried by stirring a solution of Q in a alcohol (e.g., methanol, ethanol) in the presence of palladium or platinum catalyst under an atmosphere of hydrogen gas. Treating the resulting saturated compound with TMS-I or TMS-Br in and appropriate solvent ($CH_2Cl_2$, $CHCl_3$, acetonitrile) affords R.

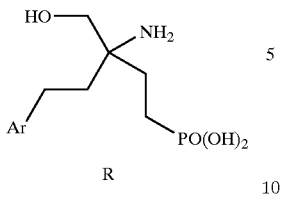

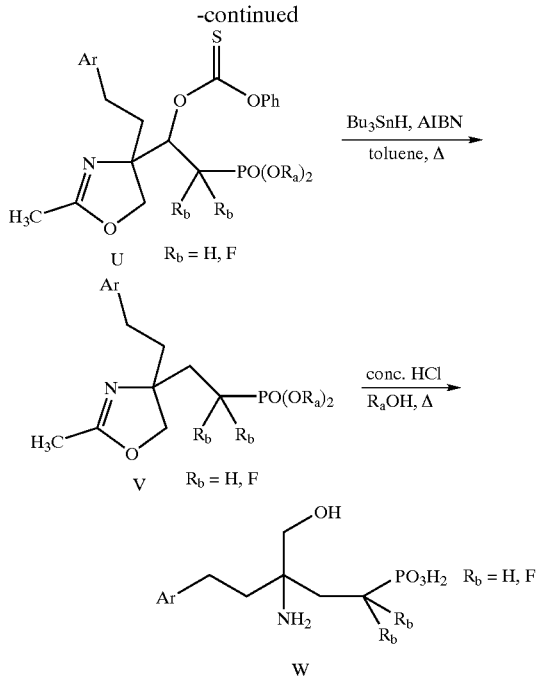

Compounds in the present invention in which $R_{1a}=R_{1b}=$ OH, $R_2$=H, $R_3$=OH and X=—$CH_2$— or —$CF_2$— can be prepared as shown in Scheme 6. Compound E can be treated with triethylorthoformate in the presence of a trialkylamine base (such as triethylamine or diisopropylethylamine) in N,N-dimethylformamide to afford oxazoline S. Oxidation under Swern conditions (oxalyl chloride/DMSO in $CH_2Cl_2$ at low temperature (<−40° C.) followed by a trialkylamine base and warming to ambient temperature) affords aldehyde T. Treating T with a dialkyl methyl phosphonate in the presence of a strong base (n-butyllithium, lithium diisopropylarnide) in an ethereal solvent (THF, diethylether, DME) at low temperature followed by quenching the resulting mixture with an aryl chiorothionoformate affords thiocarbon ate U. Reduction of U with a hydride reducing agent (e.g., tributyltin hydride, tris(trimethylsilyl)silane) in the presence of a radical initiator (e.g., AUBN, benzoyl peroxide) in an Inert solvent (e.g., benzene, toluene) at elevated temperature can give V. Concomitant hydrolysis of the oxazoline ring and the phosphon ate esters of V can be carried out by warming in a mixture of alcohol and concentrated hydrochloric acid to give W.

Scheme 6

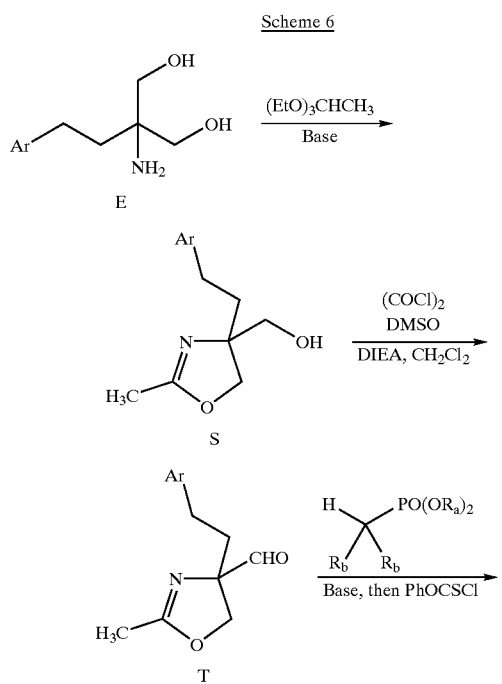

The invention is further illustrated by the following examples:

Method of Preparation

General Methods

Concentration of solutions was carried out on a rotary evaporator under reduced pressure. Conventional flash chromatography was carried out on silica gel (230–400 mesh). Flash chromatography was also carried out using a Biotage Flash Chromatography apparatus (Dyax Corp.) on silica gel (32–63 mM, 60 Å pore size) in pre-packed cartridges of the size noted. NMR spectra were obtained in $CDCl_3$ solution unless otherwise noted. Coupling constants (J) are in hertz (Hz). Abbreviations: diethyl ether (ether), triethylamine (TEA), N,N-dilsopropylethylamine (DIEA) saturated aqueous (sat'd), room temperature (rt), hour(s) (h), minute(s) (min).

HPLC Methods

HPLC A: Analytical Sales and Service Armor C8, 5μ, 4.6 mm×50 mm column, gradient 10:90→90:10 v/v $CH_3CN:H_2O$+0.05% TFA over 4 min, then hold at 90:10 v/v $CH_3CN:H_2O$+0.05% TFA for 4 min; 2.5 mL/min, 210 nm.

HPLC B: YMC ODS A, 5μ, 4.6×50 mm column, gradient 10:90→95:5 v/v $CH_3CN:H_2O$+0.05% TFA over 4.5 min, then hold at 95:5 v/v $CH_3CN:H_2O$+0.05% TFA for 1.5 min; 2.5 mL/min, 210 nm.

HPLC C: Chiral Technologies Chiralcel™ OD 4.6 mm×250 mm column, 65:35 v/v iPrOH/hexanes, 0.5 mL/min, 210 nm.

EXAMPLE 2

3-Amino-3-hydroxymethyl-5-(4-octylphenyl) pentylphoslphonic acid

Step A: (+/−)-2-Methyl-4-hydroxymethyl-4-(2-(4-octylphenyl)ethyl)oxazoline

A solution of 450 mg (1.5 mmol) of 2-amino-2-hydroxymethyl-4-(4-(octyl)phenyl)butanol, 0.32 mL (1.75 mmol) of triethylorthoacetate and 0.56 mL (3.2 mmol) of DIEA in 6 mL of DMF was stirred at 75° C. for 2 h. The mixture was cooled, partitioned between 40 mL of 3:1 v/v ether/EtOAc and water and the layers were separated. The organic layer was washed with water and dried. Flash chromatography on silica gel using 4:1 v/v $CH_2Cl_2$/EtOAc as the eluant afforded 440 mg (91%) of the title compound: Mass spectrum ($NH_3$—CI) 332 (M+H).

Step B: (+/−)-2-Methyl-4-formyl-4-(2-(4-octylphenyl)ethyl) oxazoline

A solution of 0.059 mL (0.8 mmol) of oxalyl chloride in 1.5 mL of $CH_2Cl_2$ at −78° C. was treated with 0.12 mL (1.6 mmol) of DMSO. The resulting mixture was stirred cold for 10 min, 118 mg of (+/−)-2-methyl-4-hydroxymethyl-4-(2-(4-octylphenyl)ethyl)oxazoline (from EXAMPLE 2, Step A) was added and resulting mixture was stirred cold for 30 min. TEA (0.28 mL, 2.0 mmol) was added and the resulting mixture was warmed to rt. The mixture was partitioned between 30 mL of ether and 10 mL of water. The organic layer was separated, dried and concentrated to afford 118 mg (100%) of the title compound.

Step C: Dimethyl 2-phenoxythiocarbonyloxy-(2-methyl-4-(2-(4-octylphenyl)ethyl)oxazolin-4-yl)ethylphosphonate A solution of 0.46 mL of 2 M n-butyllithium in hexanes in 4 mL of THF at −78° C. was treated with 0.10 mL (0.92 mmol) dimethyl methylphosphonate and strirred cold for 50 min. (+/−)-2-Methyl-4-formyl-4-(2-(4-octylphenyl)ethyl) oxazoline (252 mg, 0.76 mmol, from EXAMPLE 2, Step B) was added and the resulting solution was stirred cold for 5 h. The mixture was treated with 0.32 mL (2.3 mmol) of phenyl chlorothionoformate and stirred cold for 1 h. The reaction was quenched with 2 mL of sat'd $NH_4Cl$, then extracted with 30 mL of $CH_2Cl_2$. The organic layer was separated, washed with sat'd $NaHCO_3$, dried and concentrated. Flash chromatography on silica gel using hexanes/EtOAc/$CH_3CN$ as the eluant afforded 75 mg (17%) of the title compound as a mixture of isomers: Mass spectrum ($NH_3$—CI) 590 (M+H).

Step D: (+/−)-Dimethyl (2-methyl-4-(2-(4-octylphenyl) ethyl)oxazolin-4-yl)ethyl phosphonate A solution of 67 mg (0.07 mmol) of dimethyl 2-phenoxythiocarbonyloxy-(2-methyl -4-(2-(4-octylphenyl) ethyl)oxazolin-4-yl)ethylphosphonate (from EXAMPLE 2, Step C), 0.07 mL (0.27 mmol) of tributyltin hydride and 10 mg (0.06 mmol) of AIBN in 4 mL of toluene was heated at reflux for 2 h. The solution was cooled and concentrated. Flash chromatography on silica gel using $CH_2Cl_2$/EtOAc as the eluant afforded 13 mg (26%) of the title compound: Mass spectrum ($NH_3$—CI) 438 (M+H).

Step E: 3-Amino-3-hydroxymethyl-5-(4-octylphenyl) pentylphosphonic acid

A solution of 10.5 mg (0.024 mmol) of (+/−)-dimethyl (2-methyl-4-(2-(4-octylphenyl)ethyl)oxazolin-4-yl)ethyl phosphonate (from EXAMPLE 2, Step D) in 2 mL of 1:1 v/v MeOH/conc. HCL was heated at reflux for 2 h. HPLC purification afforded 6.9 mg (75%) of the title compound: Mass spectrum ($NH_3$—CI) 386 (M+H).

EXAMPLE 11

(±)-3-Amino-3-methyl-5-(4-(octyl)phenyl) pentylphosphonic acid

Step A: (±)-Diethyl 3-ethoxycarbonyl-5-(4-(octyl)phenyl) pentyl phosphonate

To a solution of triethyl 4-phosphonobutyrate (0.91 g, 3.59 mmol) in tetrahydrofuran (10 ml) at −78° C. was added a potassium bis(trimethylsilyl)amide (0.5 M in THF, 7.60 ml, 3.79 mmol). After stirring for 1 h at −78° C., a solution of trifluorormethansulfonic acid-4-ocylphenylethyl ester (prepared from 4-octylphenylethyl alcohol (1.00 g, 3.99 mmol) and trifluoromethanesulfonyl anhydride (0.74 g, 4.79 mmol) in methylene chloride in the presence of 2,6-lutidine (0.56 ml, 4.79 mmol) at 0° C.). The reaction was transferred to an ice bath and stirred for 1 h. The reaction was diluted with ethyl acetate (40 ml), washed with 2N aq HCl (40 ml), saturated aqueous sodium chloride (40 ml) and dried over magnesium sulfate. Concentration in vacuo followed by silica gel chromatography eluting with hexane/acetone (75:25) yield a colorless oil (0.74 g): $^1$H NMR (500 MHz, $CDCl_3$): δ7.07 (m, 4H), 4.05–4.17 (m, 6H), 2.54–2.60 (m, 4H), 2.43 (m, 1H), 1.57–2.04 (m, 10H), 1.24–1.34 (m, 17H), 0.87 (t, J=7.0 Hz, 3H); MS m/e 469.2 ($M^+$).

Step B: (±)-Diethyl 3-ethoxycarbonyl-3-methyl-5-(4-(octyl) phenyl)pentylphosphonate To a solution potassium bis(trimethylsilyl)amide (0.213 g, 1.068 mmol) in tetrahydrofuran (1 ml) at −78° C. was added (±)-diethyl 3-ethoxycarbonyl-5-(4-(octyl)phenyl) pentylphosphonate (0.250 g, 0.533 mmol) as a solution in 1 ml of tetrahydrofuran. After stirring for 40 minutes at −78° C., iodomethane (0.083 ml, 1.33 mmol) was added. The reaction was stirred for 1 h at −78° C. then allowed to warm to room temperature. The solution was diluted with ethyl acetate (25 ml) and washed with 2N HCl (10 ml) 5% aqueous sodium thiosulfate (10 ml), saturated aqueous sodium chloride (10 ml), dried over magnesium sulfate and concentrated to give a colorless oil (0.211 g): MS m/e 483.4 ($M^+$).

Step C: (±)-Diethyl 3-carboxy-3-methyl-5-(4-(octyl)phenyl) pentylphosphonate

To a solution of (±)-diethyl 3-ethoxycarbonyl-3-methyl-5-(4-(octyl)phenyl)pentylphosphonate (0.211 g, 0.437 mmol) in methanol (2 ml) was added 1N aqueous sodium hydroxide (1.3 ml, 1.3 mol). Tetrahydrofuran was added as necessary to keep the substrate in solution. The reaction was heated to 50° C. for 16 h then warmed to 70° and stirred at this temperature for 20 h. The reaction was diluted with ethyl acetate (30 ml) and washed with 2N aq HCl (20 ml), saturated aqueous sodium chloride (20 ml), dried over magnesium sulfate and concentrated to give a colorless oil (0.164 g): MS m/e 455.2 ($M^+$).

Step D: (±)-Diethyl 3-benzyloxycarbonylamino-3-methyl-5-(4-(octyl)phenyl)pentylphosphonic acid To a solution of (±)-diethyl 3-carboxy-3-methyl-5-(4-(octyl)phenyl)pentylphosphonate (0.165 g, 0.362 mmol) in tetrahydrofuran (1 ml) at 0° C. was added triethylamine (0.061 ml, 0.434 mmol) followed by methyl chloroformate (0.053 ml, 0.699 mmol). After stirring for 15 min, sodium azide (0.071 g, 1.08 mmol) in water (1 ml) was added. The ice bath was removed and the reaction stirred for 1 h. The reaction was diluted with ethyl acetate (25 ml) and washed with 2N aq HCl (25 ml), saturated aqueous sodium chloride (25 ml), dried over magnesium sulfate and concentrated to give a colorless oil. This oil was dissolved in toluene (1 ml), benzyl alcohol (0.056 ml, 0.543 mmol) was added and the solution heated to 90° C. for 4 h. The reaction was cooled, placed onto silica gel and eluted with hexane/acetone (70:30) to give a colorless oil (0.097 g): MS m/e 560.4 ($M^+$).

Step E: (±)-3-Amino-3-methyl-5-(4-(octyl)phenyl) pentylphosphonic acid

To a solution of (±)-diethyl 3-benzyloxycarbonylamino-3-methyl-5-(4-(octyl)phenyl)pentylphosphonic acid (0.097 g, 0.173 mmol) in methylene chloride (1 ml) was added aodotrimethylsilane (0.100 ml, 0.690 mmol). After stirring for 1 h, methanol was added (1 ml) and the reaction was concentrated. HPLC purification (YMC-Pack pro C18, 150× 20 mm, acetonitrile/water+0.1% TFA 10/90 to 0/100 over 15 minutes, 20 ml/min, 254 nM) yielded a waxy solid (0.051 g): $^1$H NMR (500 MHz, CDCl$_3$): δ7.09–7.14 (m, 4H), 2.64 (t, J=8.7 Hz, 2H), 2.56 (t, J=7.7 Hz, 3H), 1.98–2.02 (m, 2H), 1.88–1.92 (m, 2H), 1.75–1.82 (m, 2H), 1.56–1.59 (m, 2H), 1.39 (s, 3H), 1.24–1.34 (m, 12H), 0.89 (t, J=6.89 Hz, 3H); MS m/e 370.3 (M$^+$).

EXAMPLE 19

(±)-2-Amino-2-Dhosphoryloxymethyl-4-(4-(octyl) phenyl)butanol

Step A: 2-Benzyloxycarbonylamino-2-hydroxymethyl-4-(4-(octyl)phenyl)butanol

A mixture of 3.07 g (10.0 mmol) of 2-amino-2-hydroxymethyl-4-(4-(octyl)phenyl)butanol and 3.00 g (30.0 mmol) of KHCO$_3$ in 200 mL of EtOAc and 150 mL of H$_2$O was treated with 1.50 mL (10.0 mmol) of benzyl chloroformate, then stirred at rt for 2 h. The organic layer of the reaction mixture was separated, dried over MgSO$_4$ and concentrated to afford 5.29 g of the title compound: $^1$H NMR (500 Mhz) δ0.88 (t, J=6.5, 3H), 1.22–1.34 (12H), 1.55–1.60 (m, 2H), 1.87–1.91 (m, 2H), 2.53–2.59 (4H), 3.23 (br s, 2H), 3.67 (dd, J=6.5, 11.5, 1H), 3.90 (dd, J=6.5, 11.5, 1H), 5.08 (s, 2H), 5.30 (s, 1H), 7.05–7.09 (4H), 7.32–7.36 (5H); HPLC A 5.34 min.

Step B: 2-Phenyl-4-(benzyloxycarbonylamino)-4-(4-(octyl)phenyl)-1,3-dioxane

A mixture of 5.29 g (10.0 mmol) of 2-benzyloxycarbonylamino-2-hydroxymethyl-4-(4-(octyl)phenyl)butanol (from Example 2, Step A), 1.10 mL (11.0 mmol) of benzaldehyde and 95 mg, (0.05 mmol) of p-TSA. H$_2$O in 50 mL of toluene was stirred at 100° C. for 1 h. The reaction mixture was treated with an additional 2.0 mL of benzaldehyde and stirring was continued at 100° C. for 2 h. The mixture cooled to rt, then partitioned between 400 mL of ether and 150 mL of 1.0 N NaOH. The organic layer was separated, dried over MgSO$_4$ and concentrated. Chromatography on a Biotage Flash 75S cartridge using 20:1 v/v heptane/EtOAc (3 L), then 10:1 v/v heptane/EtOAc (3 L) as the eluant afforded 3.02 g of the title compound: $^1$H NMR (500 Mhz) δ0.88 (t, J=6.5, 3H), 1.22–1.36 (12H), 1.55–1.60 (m, 2H), 1.94–2.06 (m, 2H), 2.54–2.58 (4H), 3.69 (d, J=11.5, 2H), 4.31 (d, J=11.5, 2H), 5.13 (s, 2H), 5.41 (br s, 1H), 5.45 (s, 1H), 7.06–7.10 (4H), 7.29–7.40 (8H), 7.46–7.48 (2H); HPLC A 6.08 min.

Step C: ((±))-2-Benzyloxycarbonylamino-2-benzyloxymethyl-4-(4-(octyl)phenyl)butanol A solution of 3.90 g (7.4 mmol) of 2-phenyl-4-(benzyloxycarbonylamino)-4-(4-(octyl)phenyl)-1,3-dioxane (from Example 2, Step B) and 2.18 g (37.0 mmol) of BH$_3$.NHMe$_2$ in 150 mL of CH$_2$Cl$_2$ at –78° C. was treated with 4.70 mL (37.0 mmol) of BF$_3$. Et$_2$O. The resulting mixture was allowed to warm to –5° C. and was stirred for 2 h. The reaction was poured into 25 mL of 1.0 N NaOH and the resulting mixture was extracted with 100 mL of CH$_2$Cl$_2$. The extract was separated and dried over MgSO$_4$. The aqueous layer was extracted with 200 mL of ether. The ether extract was dried and the two organic extracts were combined and concentrated. Chromatography on a Biotage 75S cartridge using 6:1 v/v heptane/acetone as the eluant afforded 3.63 g of the title compound. ESI-MS 532 (M+H); HPLC A: 5.98 min; HPLC B: 5.32 min.

Step D: (±)-1-Dibenzyloxyphosphoryloxy-2-benzyloxycarbonylamino-2-benzyloxymethyl-4-(4-(octyl)phenyl)butane A solution of 2.90 g (5.4 mmol) of (±)-2-benzyloxycarbonylamino-2-benzyloxymethyl-4-(4-(octyl)phenyl)butanol (from Example 2, Step D) and 2.00 mL (6.0 mmol) of dibenzyl diisopropylphosphoramidite in 40 mL of CH$_2$Cl$_2$ at 0° C. was treated with 117 mg (8.2 mmol) of 1H-tetrazole. The resulting mixture was stirred at rt for 1.25 h, then cooled to –78° C. MCPBA (2.0 g, ~8.2 mmol) was added, the cooling bath was removed and the reaction was stirred at ambient temperature for 45 min. The reaction was quenched with 50 mL of sat'd NaHCO$_3$, then extracted with 200 ML of CH$_2$Cl$_2$. The extract was separated and dried over MgSO$_4$. The aqueous layer was extracted with 200 mL of ether. The ether extract was dried and the two organic extracts were combined and concentrated. Chromatography on a Biotage 75S cartridge using 8:1 v/v heptane/acetone (4.5 L), then 4:1 v/v heptane/acetone (2 L) as the eluant afforded 4.25 g of the title compound: $^1$H NMR (500 Mhz) δ0.88 (t, J=6.5, 3H), 1.22–1.36 (12H), 1.55–1.61 (m, 2H), 1.94–2.04 (m, 1H), 2.08–2.18 (m, 1H), 2.47 (app t, J=8.5, 1H), 2.55 (app t, J=7.5, 1H), 3.54 (AB q, J=26.0, 2H), 4.18–4.25 (m, 2H), 4.44 (s, 2H), 4.98 (s, 2H), 5.00 (s, 2H), 5.03 (s, 2H), 5.11 (br s, 1H), 6.96–7.06 (8H), 7.24–7.36 (36H); HPLC A: 6.31 min.

Step E: (±)-2-Amino-2-phosphoryloxymethyl-4-(4-(octyl)phenyl)butanol

Sodium metal (200 mg, 8.3 mmol) was added to 10 mL of liquid ammonia at –33° C. The resulting dark blue mixture was stirred for 30 min, then treated with a solution of 118 mg (0.15 mmol) of (+)-1-dibenzyloxyphosphoryloxy-2-benzyloxycarbonylamino-2-benzyloxymethyl-4-(4-(octyl)phenyl)butane (from Example 2, Step D) in 1 mL of THF. The cooling bath was removed and the reaction mixture was stirred at ambient temperature for 18 h. The reaction was quenched with 40 mL of H$_2$O, then extracted with 40 mL of ether. The aqueous layer was separated and neutralized (pH 7) with 1.0 N HCl. The precipitate was filtered, rinsed with H20, then MeOH and dried to afford 49 mg of the title compound: $^1$H NMR (500 Mhz, CD$_3$OD+NaOD) δ0.89 (t, J=7.0, 3H), 1.22–1.36 (12H), 1.43–1.62 (m, 2H), 1.86–1.94 (m, 2H), 2.55 (app t, J=7.5, 2H), 2.63–2.68 (m, 2H), 3.66 (app q, J=11.0, 1H), 3.88 (dd, J=, 6.5, 11.5, 1H), 3.96 (dd, J=6.5, 11.5), 7.06 (d, J=7.5, 2H), 7.13 (d, J=7.5, 2H); ESI-MS 388 (M+H); HPLC A 3.96min; HPLC B 2.84 min.

EXAMPLE 20

(R)-2-Amino-2-phosphoryloxymethyl-4-(4-(octyl) phenyl)butanol and (S)-2-Amino-2-phosphoryloxymethyl-4-(4-(octyl)phenyl)butanol Step A: Resolution of (±)-1-dibenzyloxyphosphoryloxy-2-benzyloxycarbonylamino-2-benzyloxymethyl4-(4-(octyl)phenyl)butane The enantiomers of (±)-1-dibenzyloxyphosphoryloxy-2-benzyloxycarbonylamino-2-benzyloxymethyl-4-(4-(octyl)phenyl)butane (from Example 2, Step D) were resolved using preparative chiral HPLC. Conditions: Chiral Technologies Chiralcel™ OD 2 cm×25 cm column, 60:40 v/v hexanes/iPrOH, 9.0 mL/min, 210 nm. For the faster eluting enantiomer (Enantiomer 1): HPLC C 16.7 min. For the slower eluting enantiomer (Enantiomer 2): HPLC C 24.0 min.

Step B: 2-Amino-2-phosphoryloxymethyl-4-(4-(octyl) phenyl)butanol (Enantiomer 1 and Enantiomer 2)

The title compound (Enantiomer 1) was obtained from 1-dibenzyloxyphosphoryl oxy-2-benzyloxycarbonylamino-2-benzyloxymethyl-4-(4-(octyl)phenyl)butane (Enantiomer 1 from Example 20, Step A) using a procedure analogous to that described in Example 2, Step E: ESI-MS 388 (M+H); HPLC A 3.96 min; HPLC B 2.84 min.

The title compound (Enantiomer 2) was obtained from 1-dibenzyloxyphosphoryloxy-2-benzyloxycarbonylamino-2-benzyloxymethyl-4-(4-(octyl)phenyl)butane (Enantiomer 2 from Example 20, Step A) using a procedure analogous to that described in Example 2, Step E: ESI-MS 388 (M+H); HPLC A 3.96 min; HPLC B 2.84 min.

EXAMPLE 21

1,1-Difluoro-3-amino-3-hydroxymethyl-5-(4-octylphenyl)pentylphosphonic acid

The title compound was prepared from 2-amino-2-hydroxymethyl-4-(4-(octyl)phenyl)butanol (FrY 720) using procedures analogous to those described in EXAMPLE 2, except that lithium diisopropylamide was substituted for n-butyllithium in Step C and diethyl difluoromethylphosphonate was substituted for dimethyl methylphosphonate in Step C: Mass spectrum ($NH_3$—CI) 422 (M+H).

The compounds of the present invention can also be used as a screening tool to identify candidate compounds that bind to G-protein-coupled receptors comprising the following steps:

(1) providing a whole cell expressing G-protein-coupled receptors or membranes derived therefrom;
(2) contacting said cell or membrane with a compound of formula A and the candidate compound; and
(3) determining the amount of binding of said candidate compound by ascertaining the relative activity of the compound of formula A in the presence of the candidate compound.

What is claimed is:

1. A compound represented by formula 1:

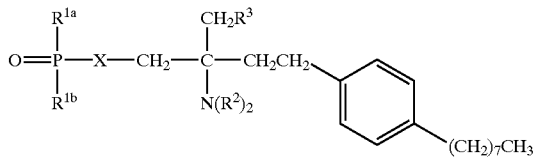

or a pharmaceutically acceptable salt or hydrate thereof, wherein:

X is O, S, $NR^1$ or $(CH_2)_{1-2}$, optionally substituted with 1–4 halo groups;
$R^1$ is H, $C_{1-4}$ alkyl or $haloC_{1-4}$ alkyl;
$R^{1a}$ is H, OH, $C_{1-4}$ alkyl, or $OC_{1-4}$ alkyl, the alkyl and alkyl portions being optionally substituted with 1–3 halo groups;
$R^{1b}$ represents H, OH, $C_{1-4}$ alkyl or $haloC_{1-4}$ alkyl;
$R^2$ is H, $C_{1-4}$ alkyl or $haloC_{1-4}$ alkyl, and
$R^3$ is H, OH, halo, $OC_{1-4}$ alkyl or $O-haloC_{1-4}$ alkyl.

2. A compound in accordance with claim 1 wherein X is O or $(CH_2)_{1-2}$, optionally substituted with 1–4 halo groups.

3. A compound in accordance with claim 2 wherein X is O or $CH_2$.

4. A compound in accordance with claim 3 wherein X is O.

5. A compound in accordance with claim 1 wherein $R^{1a}$ is H or OH.

6. A compound in accordance with claim 1 wherein $R^{1b}$ represents H or OH.

7. A compound in accordance with claim 1 wherein $R^3$ is H, OH, halo, $OC_{1-4}$ alkyl or $O-haloC_{1-4}$ alkyl.

8. A compound in accordance with claim 1 wherein $R^2$ is H or $C_{1-4}$ alkyl.

9. A compound in accordance with claim 1 wherein:
X is O or $(CH_2)_{1-2}$, optionally substituted with 1–4 halo groups;
$R^{1a}$ is H or OH;
$R^{1b}$ represents H or OH;
$R^2$ is H, $C_{1-4}$ alkyl or $haloC_{1-4}$ alkyl, and
$R^3$ is H, OH, halo, $OC_{1-4}$ alkyl or $O-haloC_{1-4}$ alkyl.

10. A compound in accordance with claim 1 in accordance with the following table:

TABLE 1

1a

| Cpd | X | $R^2/R^2$ | $R^3$ |
|---|---|---|---|
| 1 | O | H/H | OH |
| 2 | $CH_2$ | H/H | OH |
| 3 | $CH_2CH_2$ | H/H | OH |
| 4 | O | $H/CH_3$ | OH |
| 5 | $CH_2$ | $H/CH_3$ | OH |
| 6 | $CH_2CH_2$ | $H/CH_3$ | OH |
| 7 | O | $CH_3/CH_3$ | OH |
| 8 | $CH_2$ | $CH_3/CH_3$ | OH |
| 9 | $CH_2CH_2$ | $CH_3/CH_3$ | OH |
| 10 | O | H/H | H |
| 11 | $CH_2$ | H/H | H |
| 12 | $CH_2CH_2$ | H/H | H |
| 13 | O | $H/CH_3$ | H |
| 14 | $CH_2$ | $H/CH_3$ | H |
| 15 | $CH_2CH_2$ | $H/CH_3$ | H |
| 16 | O | $CH_3/CH_3$ | H |
| 17 | $CH_2$ | $CH_3/CH_3$ | H |
| 18 | $CH_2CH_2$ | $CH_3/CH_3$ | H | or a pharmaceutically acceptable salt or hydrate thereof.

11. A compound in accordance with claim 10 wherein X represents O, each $R^2$ represents H and $R^3$ represents OH.

12. A method of treating or preventing an immunoregulatory abnormality in a mammalian patient in need of such treatment or prevention, comprising administering to said patient a compound in accordance with claim 1 in an amount that is effective for treating or preventing said immunoregulatory abnormality.

13. A method in accordance with claim 12 wherein the immunoregulatory abnormality is an autoimmune or chronic inflammatory disease selected from the group consisting of: systemic lupus erythematosis, chronic rheumatoid arthritis, type I and II diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma.

14. A method in accordance with claim 13 wherein the immunoregulatory abnormality is bone marrow or organ transplant rejection.

15. A method in accordance with claim 11 wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, Lichen planus, Pemphigus, bullous pemphigoid, Epidermolysis bullosa, urticaria, angioedemas, vasculitis, erythema, cutaneous eosinophilia, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyperresponsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, Coeliac diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulganis, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy; Pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis, pigentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

16. A method of suppressing the immune system in a mammalian patient in need of immunosuppression comprising administering to said patient an immunosuppressing effective amount of a compound of claim 1.

17. A pharmaceutical composition comprised of a compound in accordance with claim 1 in combination with a pharmaceutically acceptable carrier.

18. A compound represented by formula A:

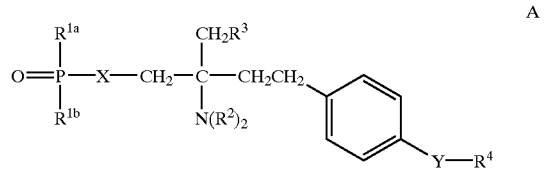

or a pharmaceutically acceptable salt or hydrate thereof, wherein:

X is O, S, $NR^1$ or $(CH_2)_{1-2}$, optionally substituted with 1–4 halo groups;

$R^1$ is H, $C_{1-4}$ alkyl or halo$C_{1-4}$ alkyl;

$R^{1a}$ is H, OH, $C_{1-4}$ alkyl, or $OC_{1-4}$ alkyl, the alkyl and alkyl portions being optionally substituted with 1–3 halo groups;

$R^{1b}$ represents H, OH, $C_{1-4}$ alkyl or halo$C_{1\ 4}$ alkyl;

each $R^2$ is independently selected from the group consisting of: H, $C_{1-4}$ alkyl and halo$C_{1-4}$ alkyl, $R^3$ is H, OH, halo, $C_{1-4}$alkyl, $OC_{1-4}$alkyl, O-halo$C_{1-4}$alkyl or hydroxy $C_{1-4}$alkyl, Y is selected from the group consisting of: —$CH_2$—, —C(O)—, —CH(OH)—, —C(=NOH)—, O and S, and $R^4$ is selected from the group consisting of: $C_{4-14}$alkyl and $C_{4-14}$alkenyl.

19. A compound in accordance with claim 18 wherein X is O or $(CH_2)_{1-2}$, optionally substituted with 1–4 halo groups.

20. A compound in accordance with claim 19 wherein X is O or $CH_2$.

21. A compound in accordance with claim 20 wherein X is O.

22. A compound in accordance with claim 18 wherein $R^{1a}$ is H or OH.

23. A compound in accordance with claim 18 wherein $R^{1b}$ represents H or OH.

24. A compound in accordance with claim 18 wherein $R^3$ is H or OH.

25. A compound in accordance with claim 18 wherein $R^2$ is H or $C_{1-4}$ alkyl.

26. A compound in accordance with claim 18 wherein:

X is O or $(CH_2)_{1-2}$, optionally substituted with 1–4 halo groups;

$R^{1a}$ is H or OH;

$R^{1b}$ represents H or OH;

each $R^2$ is independently selected from the group consisting of: H, $C_{1-4}$ alkyl or halo$C_{1-4}$ alkyl, and R³ is H, OH, halo, C$_{1-4}$alkyl, OC$_{1-4}$alkyl, O-haloC$_{1-4}$alkyl or hydroxyC$_{1-4}$alkyl.

27. A compound according to claim 18 wherein Y is —CH$_2$— and R⁴ is heptyl.

28. A compound according to claim 27 wherein:
X is O or CH$_2$, optionally substituted with 1–2 halo groups;
R$^{1a}$ is OH;
R$^{1b}$ is OH;
each R² is H, and
R³ is H or OH.

29. A compound according to claim 18 selected from the group consisting of:
(a) 3-Amino-3-hydroxymethyl-5-(4-octylphenyl) pentylphosphonic acid;
(b) 3-Amino-3-methyl-5-(4-(octyl)phenyl) pentylphosphonic acid; and
(c) 1,1-Difluoro-3-amino-3-hydroxymethyl-5-(4-octylphenyl)pentylphosphonic acid.

30. A compound according to claim 18 which is 2-Amino-2-phosphoryloxymethyl-4-(4-(octyl)phenyl)butanol.

31. A compound according to claim 18 which is (R)-2-Amino-2-phosphoryloxymethyl-4-(4-(octyl)phenyl) butanol.

32. A compound which is (S)-2-Amino-2-phosphoryloxymethyl-4-(4-(octyl)phenyl)butanol.

33. A method of treating or preventing an immunoregulatory abnormality in a mammalian patient in need of such treatment or prevention, comprising administering to said patient a compound in accordance with claim 18 in an amount that is effective for treating or preventing said immunoregulatory abnormality.

34. A method in accordance with claim 33 wherein the immunoregulatory abnormality is an autoimmune or chronic inflammatory disease selected from the group consisting of: systemic lupus erythematosis, chronic rheumatoid arthritis, type I and II diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma.

35. A method in accordance with claim 33 wherein the immunoregulatory abnormality is bone marrow or organ transplant rejection.

36. A method in accordance with claim 33 wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalo myelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, Lichen planus, Pemphigus, bullous pemphigoid, Epidermolysis bullosa, urticaria, angioedemas, vasculitis, erythema, cutaneous eosinophilia, Lupus erythematosus, acne, Alopecia areata, keratoconjunctivitis, vernal conjunctivitis, uveitis associated with Behcet's disease, keratitis, herpetic keratitis, conical cornea, dystrophia epithelialis comeae, corneal leukoma, ocular pemphigus, Mooren's ulcer, Scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyperresponsiveness, bronchitis, gastric ulcers, vascular damage caused by ischemic diseases and thrombosis, ischemic bowel diseases, inflammatory bowel diseases, necrotizing enterocolitis, intestinal lesions associated with thermal bums, Coeliac diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth muscular dystrophy; Pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis, pigentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C$_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

37. A method of suppressing the immune system in a mammalian patient in need of immunosuppression comprising administering to said patient an immunosuppressing effective amount of a compound of claim 18.

38. A pharmaceutical composition comprised of a compound in accordance with claim 18 in combination with a pharmaceutically acceptable carrier.

* * * * *